United States Patent [19]

Yates

[11] Patent Number: 4,677,414

[45] Date of Patent: Jun. 30, 1987

[54] OXYGEN SENSOR

[75] Inventor: Anthony Yates, Sutton Coldfield, England

[73] Assignee: Lucas Electrical Electronics & Systems Ltd., Birmingham, England

[21] Appl. No.: 680,946

[22] Filed: Dec. 12, 1984

[30] Foreign Application Priority Data

Dec. 23, 1983 [GB] United Kingdom ............... 8334391
Sep. 29, 1984 [GB] United Kingdom ............... 8424662

[51] Int. Cl.$^4$ .......................................... H01L 7/00
[52] U.S. Cl. ...................................... 338/34; 338/36
[58] Field of Search .......................... 338/34, 36, 35; 252/62.63; 423/594; 422/94, 98; 73/27 R, 23; 324/71.5

[56] References Cited

U.S. PATENT DOCUMENTS 4,453,397 6/1984 Ohta et al. ........................ 338/34 X
4,454,494 6/1984 Williams et al. ..................... 338/34

OTHER PUBLICATIONS

Sisler et al., *College Chemistry, A Systematic Approach*, New York, The MacMillan Company, 1953, p. 72.

Primary Examiner—Harold Broome
Assistant Examiner—M. M. Lateef
Attorney, Agent, or Firm—Trexler, Bushnell, Giangiorgi & Blackstone, Ltd.

[57] ABSTRACT

An oxygen sensor which exhibits a change in electrical resistance as a function of oxygen partial pressure, comprises at least one of strontium ferrate ($SrFeO_{3-x}$), barium ferrate ($BaFeO_{3-x}$), and strontium barium ferrate ($Sr_{1-b}Ba_bFeO_{3-x}$), where x is a variable and determines the degree of oxygen deficiency of the oxide, and b is 0 to 1, in which part of the iron in the ferrate lattice has been replaced by at least one element selected from the group consisting of zirconium, hafnium and tin.

9 Claims, 10 Drawing Figures

OXYGEN SENSOR

This invention relates to sensors for the measurement of oxygen partial pressures particularly, but not exclusively, in the exhaust gases of spark ignition internal combustion engines supplied with lean fuel/air mixtures, that is mixtures in which the fuel: air ratio is less than the stoichiometric combustion ratio of approximately 1:14 by weight.

It has previously been proposed in U.S. Pat. No. 4454494 to provide an oxygen sensor comprising a strontium, barium or strontium/barium ferrate wherein the iron in the ferrate lattice has been replaced by an element of valency greater than 3. Examples of such an element of valency greater than 3 are given as titanium, cerium, tantalum and niobium.

We have now found surprisingly that the use of zirconium, hafnium and/or tin as replacement for part of the iron in the ferrate lattice of a strontium, barium or strontium/barium ferrate oxygen sensor gives significantly improved results in respect of temperature dependency and hysteresis effects and in addition hafnium exhibits decreased conductivity and increased durability in acidic atmospheres.

Thus, according to the present invention there is provided an oxygen sensor exhibiting a change in electrical resistance as a function of oxygen partial pressure, comprising at least one of strontium ferrate ($SrFeO_{3-x}$), barium ferrate ($BaFeO_{3-x}$), and strontium barium ferrate ($Sr_{1-b}Ba_bFeO_{3-x}$), where x is a variable and determines the degree of oxygen deficiency of the oxide, and its value depends upon temperature and oxygen partial pressure, but it generally falls within the range 0 to 0.5 and b is 0 to 1, in which part of the iron in the ferrate lattice has been replaced by at least one element selected from the group consisting of zirconium, hafnium and tin.

The substituted ferrate described above preferably obeys the formula:

$JFe_{1-y}A_yO_{3-x}$, where J is selected from the group consisting of Sr, Ba and $Sr_{1-b}Ba_b$, A is selected from the group consisting of Zr, Hf and Sn, x is as defined above and y is greater than 0 but less than 0.9. Preferably, y is greater than or equal to 0.1 but less than or equal to 0.7, and where b is as defined above.

It is also possible for some of said at least one element selected from the group consisting of zirconium, hafnium and tin to be substituted by at least one other tetravalent element such that in the above composition equation ($A_{y-z}D_z$) may be substituted for $A_y$ where D is any tetravalent element or combination of tetravalent elements and z is less than y. Thus, such a ferrate obeys the formula $JFe_{1-y}A_{y-z}D_zO_{3-x}$. Said at least one other tetravalent element may be selected from titanium and cerium.

It is also possible to use a ferrate in which part of the iron has been replaced by said at least one element and by at least one pentavalent element, for example, a substituted ferrate of the formula $JFe_{1-y}A_rQ_sO_{3-x}$, where J, A and x are as defined hereinabove, y is greater than 0 and less than or equal to 0.5, Q is at least one pentavalent element and r+s=y. In a convenient embodiment, y=0.5, and r and s are both 0.25. Said at least one pentavalent element may be selected from tantalum and niobium.

Said at least one element selected from the group consisting of zirconium, hafnium and tin, and said pentavalent elements may be partly replaced by a trivalent or divalent element.

Conveniently, said trivalent or divalent element is selected from aluminium, cobalt and nickel.

In the accompany drawings.

EXAMPLE 1

A powder mixture was prepared consisting of 1 mole of strontium carbonate of mean particle size 50 to 70 microns, 0.25 mole of zirconium oxide again of mean particle size 50 to 70 microns, and 0.375 mole of calcined ferric oxide of mean particle size 25 to 40 microns. Each of the samples was that supplied by British Drug Houses Ltd., as the reagent grade material and, before mixing; each sample was subjected to impurity analysis by spark emission spectrography. In the case of the strontium carbonate, the main impurities were 0.4% by weight barium, 150 ppm by weight calcium and 100 ppm by weight silicon, whereas in the case of the zirconium oxide, the major impurities were 0.2% by weight hafnium, 250 ppm by weight calcium and 150 ppm by weight silicon. The major impurities in the ferric oxide sample were 0.35% by weight calcium, 0.16% by weight zinc, 0.14% by weight lead, 700 ppm by weight aluminium, 460 ppm by weight nickel, 400 ppm by weight manganese, 280 ppm by weight molybdenum, and 100 ppm by weight tin.

The mixture was ball-milled in the presence of acetone in a synthetic resin pot using alumina balls for 12 hours to obtain a very homogenous mix. The resultant mix was then dried at 100° C. for 2 hours to give a fine, homogenously mixed powder which was ground and then passed through a 75 micron seive. The powder was then placed in an alumina boat in a furnace which was slowly heated (i.e. of the order of up to 10° C. per minute) to 1300° C. in an air atmosphere. The furnace was held at this temperature for 16 hours, whereafter the product so formed was allowed to furnace cool to room temperature before being removed from the furnace.

The product removed from the furnace was in the form of agglomerates and was ground before being subjected to X-ray diffraction which showed that zirconium had entered the ferrate lattice. A sample of the ground powder was then placed in a tool steel die and punch assembly and cold pressed at 345 MNm$^{-2}$ into a cylindrical pellet 10 mm in diameter and 3.8 mm high. After removal from the die the pellet was sintered at 1300° C. for 24 hours and, when the pellet had cooled, electrical contact areas were provided on the planar end surfaces of the pellet. To produce the contact areas, a gold paste was initially applied to the end surfaces, whereafter gold electrodes were attached and the assembly was fired at 1000° C. for four hours to effect joining of the electrodes.

Figure 1:
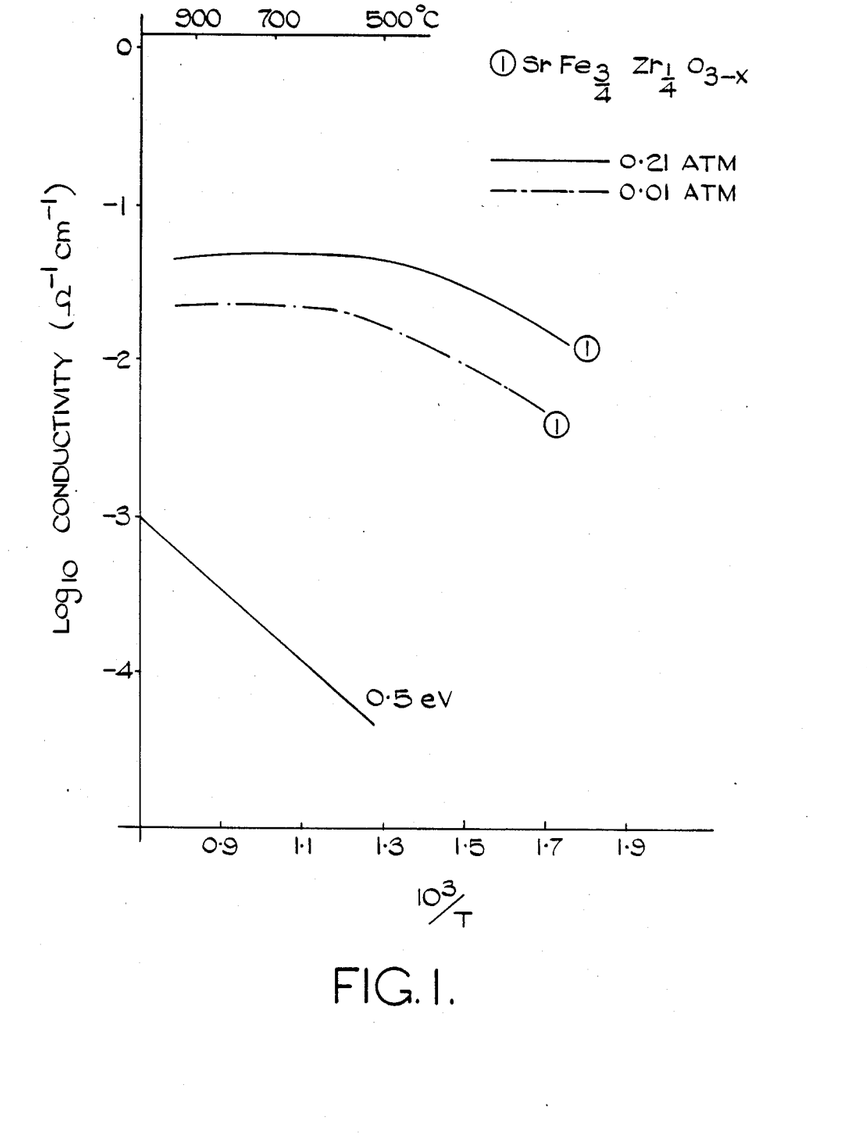
FIG. 1 is a graph plotting log $_{10}$ conductivity (ohm$^{-1}$.cm$^{-1}$) against $10^3$/temperature, T(K) for a strontium ferrate of composition $SrFe_{3/4}Zr_{1/4}O_{3-x}$ at different oxygen partial pressures.

The resultant pellet was then mounted in an alumina jig and connected to an LCR bridge to enable electrical conductivity measurements to be made. The jig was then placed in a furnace and, with a constant air atmosphere being maintained in the furnace, the electrical conductivity of the sample was measured at varying temperatures between 300° C. and 1000° C. The results are shown in FIG. 1 by the continuous line numbered 1. The procedure was then repeated with the furnace atmosphere being maintained constant at an oxygen partial pressure of $1 \times 10^{-2}$ atm, with the results obtained being shown by the chain dotted line numbered 1 in FIG. 1.

By inspection of the gradient of the lines 1 in FIG. 1, it will be seen that the $E_a$ value for the sample was less than 0.5 eV for both atmospheres and over the entire temperature range investigated. In this respect, it is to be appreciated that the line marked "0.5 ev" is merely intended to show the gradient corresponding to an $E_a$ value of 0.5 eV and hence its position on the graph is arbitrary. It will also be seen from FIG. 1 that, for a given temperature, there was a noticeable difference between the electrical conductivity measured in air (corresponding to an oxygen partial pressure value of 0.21 atm) and the oxygen-depleted atmosphere (i.e. $1 \times 10^{-2}$ atm), particularly at the lower temperature in the range investigated.

EXAMPLES 2 and 3.

Figure 2:
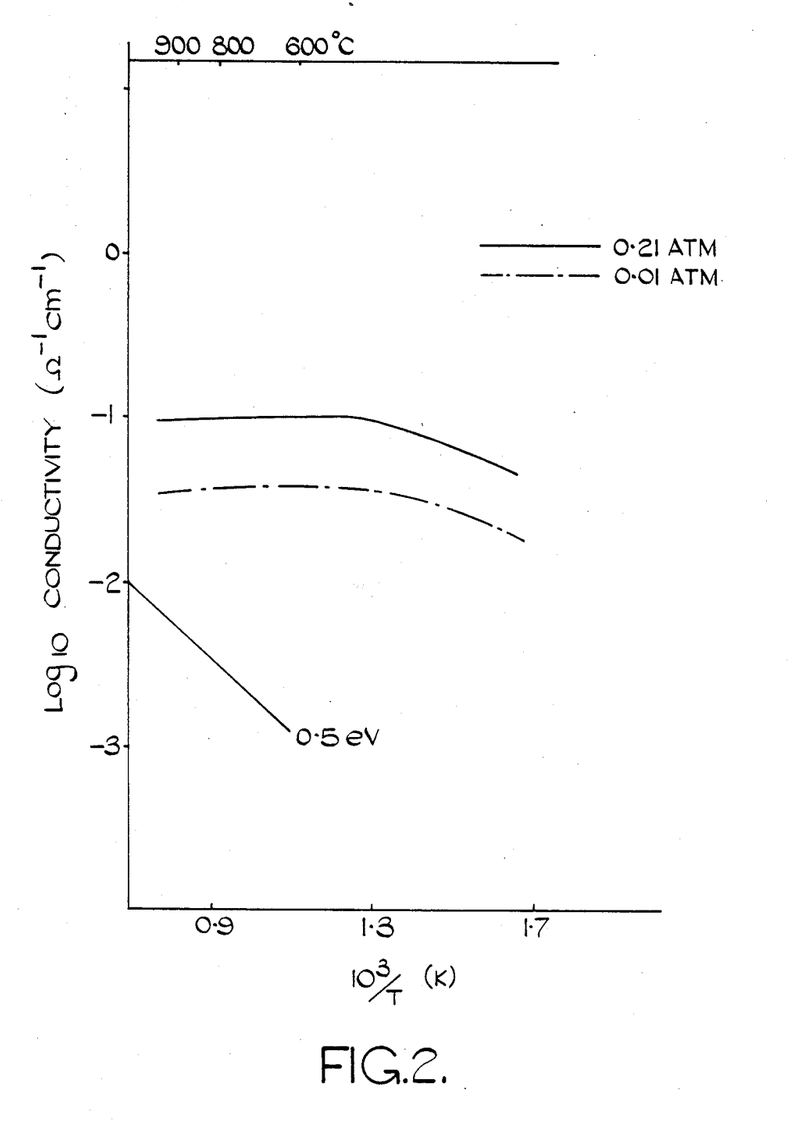
FIG. 2 is a graph as in FIG. 1 for a barium ferrate of composition $BaFe_{0.9}Zr_{0.1}O_3$.
Figure 3:
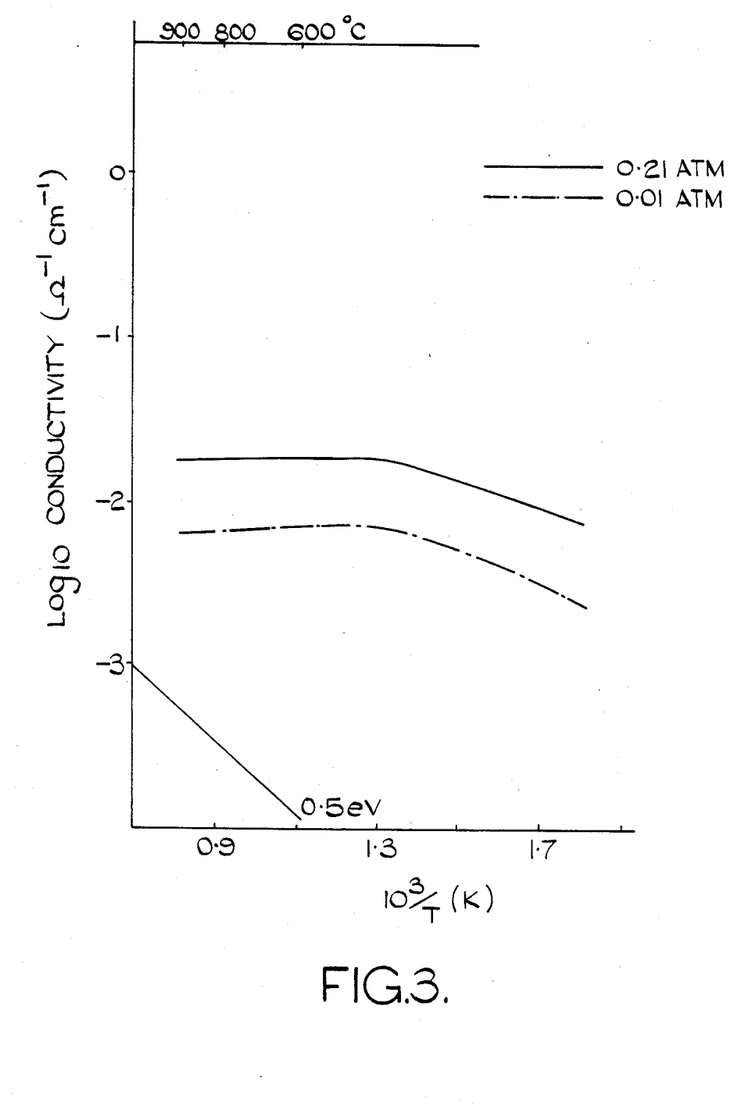
FIG. 3 is a graph as in FIG. 1 for a barium ferrate of composition $BaFe_{0.3}Zr_{0.7}O_3$.

The procedure described in Example 1 was repeated for mixtures having different relative proportions of zirconium oxide and ferric oxide so as to vary the amount of zirconium substitution in a barium ferrate lattice. The composition of these further mixtures and the resultant ferrates are shown in the Table below. The results obtained are shown in FIGS. 2 and 3.

TABLE

| Example No. | BaCO$_3$ mole | ZrO$_2$ mole | Fe$_2$O$_3$ mole | Ferrate |
|---|---|---|---|---|
| 2 | 1 | 0.1 | 0.45 | BaFe$_{0.9}$Zr$_{0.1}$O$_3$ |
| 3 | 1 | 0.7 | 0.15 | BaFe$_{0.3}$Zr$_{0.7}$O$_3$ |

The barium carbonate used in Examples 2 and 3 was supplied by British Drug Houses and had the following impurities: 0.3% by weight strontium, 200 ppm by weight calcium and 70 ppm by weight silicon.

The procedure of the first Example was repeated with starting materials from different suppliers (and hence having different impurities) but the results obtained showed no significant variation from those shown in the Figures.

Figure 4:
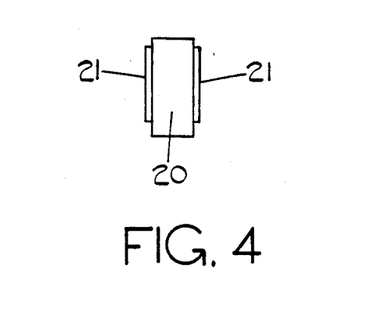
FIG. 4 is a side view of an oxygen sensor of the present invention.

Referring now to FIG. 4, the oxygen sensor illustrated therein is produced as described in Example 1 above and comprises a body 20 formed of a pellet of the substituted ferrate material. The body 20 is of right cylindircal shape with a circular cross-section and has gold electrodes 21 secured to opposite axial ends thereof by a platinum paste (not shown). This oxygen sensor is arranged to be used by clamping it between a pair of spring loaded electrical contacts which engage the electrodes 21. The electrical contacts are mounted on a support which also carries a heater and a temperature sensor which, in use, are disposed adjacent the oxygen sensor.

EXAMPLE 4

A powder mixture was prepared consisting of 1 mole of barium carbonate of mean particle size 50 to 70 microns, 0.25 mole of hafnium oxide again of mean particle size 50 to 70 microns, and 0.375 mole of calcined ferric oxide of mean particle size 25 to 40 microns. Each of the samples was that supplied by British Drug Houses Ltd., as the reagent grade material and, before mixing each sample was subjected to impurity analysis by spark emission spectrography. In the case of the barium carbonate, the main impurities were 0.4% by weight strontium, 150 ppm by weight calcium and 100 ppm by weight silicon, whereas in the case of the hafnium oxide, the major impurities were 0.2% by weight zirconium, 250 ppm by weight calcium and 150 ppm by weight silicon. The major impurities in the ferric oxide sample were 0.35% by weight calcium, 0.16% by weight zinc, 0.14% by weight lead, 700 ppm by weight aluminium, 460 ppm by weight nickel, 400 ppm by weight manganese, 280 ppm by weight molybdenum, and 100 ppm by weight tin.

The mixture was ball-milled in the presence of acetone in a synthetic resin pot using alumina balls for 12 hours to obtain a very homogenous mix. The resultant mix was then dried at 100° C. for 2 hours to give a fine, homogenously mixed powder which was ground and then passed through a 75 micron seive. The powder was then placed in an alumina boat in a furnace which was slowly heated (i.e. of the order of up to 10° C. per minute) to 1300° C. in an air atmosphere. The furnace was held at this temperature for 16 hours, whereafter the product so formed was allowed to furnace cool to room temperature before being removed from the furnace. The product removed from the furnace was in the form of agglomerates and was ground before being subjected to X-ray diffraction which showed that hafnium had entered the ferrate lattice. A sample of the ground powder was then placed in a tool steel die and punch assembly and cold pressed at 345 MNm$^{-2}$ into a cylindrical pellet 10 mm in diameter and 3.8 mm high. After removal from the die the pellet was sintered at 1300° C. for one hour and, when the pellet had cooled, electrical contact areas were provided on the planar end surfaces of the pellet. To produce the contact areas, a gold paste was initially applied to the end surfaces, whereafter gold electrodes were attached and the assembly was fired at 1000° C. for four hours to effect joining of the electrodes.

Figure 5:
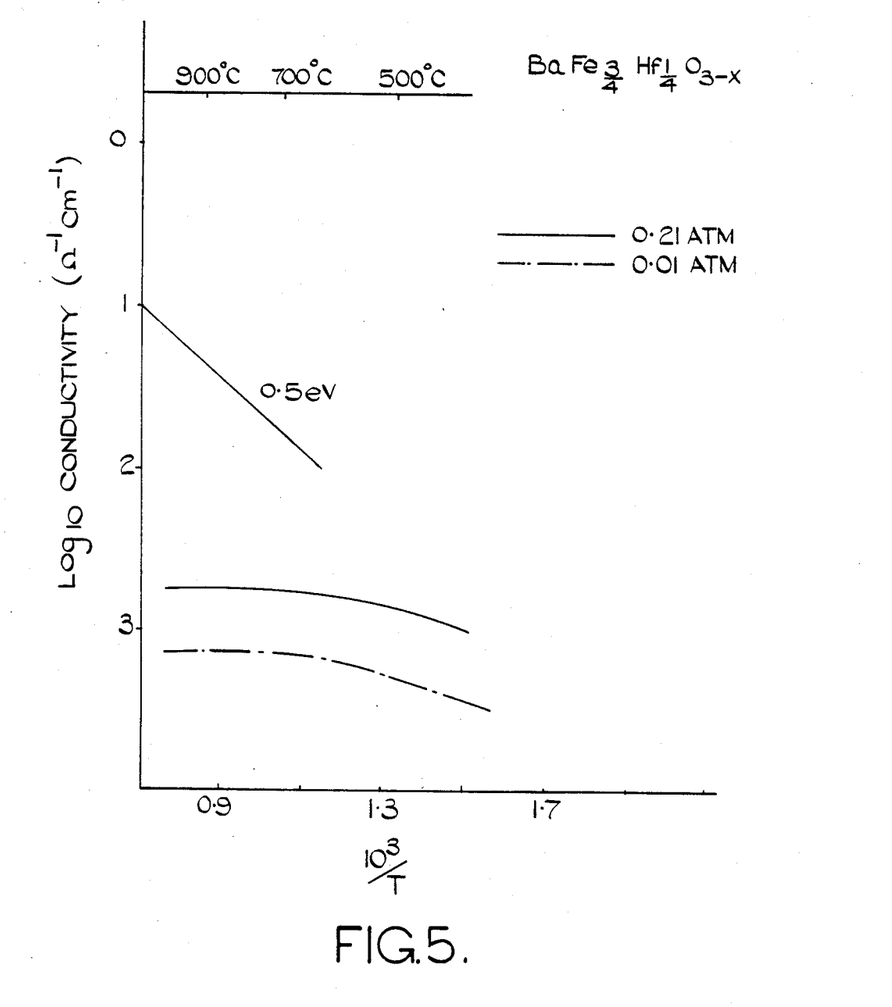
FIG. 5 is a graph plotting log $_{10}$ conductivity (ohm$^{-1}$. cm$^{-1}$) against $10^3$/temperature, T (K) for a barium ferrate of composition $BaFe_{3/4}Hf_{1/4}O_{3-x}$ at different oxygen partial pressures.

The resultant pellet was then mounted in an alumina jig and connected to an LCR bridge to enable electrical conductivity measurements to be made. The jig was then placed in a furnace and, with a constant air atmosphere being maintained in the furnace, the electrical conductivity of the sample was measured at varying temperatures between 300° C. and 1000° C. The results are shown in FIG. 5 by the continuous line numbered 1. The procedure was then repeated with the furnace atmosphere being maintained constant at an oxygen partial pressure of $1\times 10^{-2}$ atm, with the results obtained being shown by the chain dotted line numbered 1 in FIG. 5.

By inspection of the gradient of the lines 1 in FIG. 5, it will be seen that the $E_a$ value for the sample was less than 0.5 eV for both atmospheres and over the entire temperature range investigated. In this respect, it is to be appreciated that the line marked "0.5 ev" is merely intended to show the gradient corresponding to an $E_a$ value of 0.5 eV and hence its position on the graph is arbitrary. It will also be seen from FIG. 5 that, for a given temperature, there was a noticeable difference between the electrical conductivity measured in air (corresponding to an oxygen partial pressure value of 0.21 atm) and the oxygen-depleted atmosphere (i e $1\times 10^{-2}$ atm), particularly at the lower temperature in the range investigated.

EXAMPLES 5 AND 6

The procedure described in Example 4 was repeated for mixtures having different relative proportions of hafnium oxide and ferric oxide so as to vary the amount of hafnium substitution in a barium ferrate lattice. The composition of these further mixtures and the resultant ferrates are shown in the Table below. The results obtained are shown in FIGS. 6 and 7.

TABLE

| Example No. | $BaCO_3$ mole | $HfO_2$ mole | $Fe_2O_3$ mole | Ferrate |
|---|---|---|---|---|
| 5 | 1 | 0.1 | 0.45 | $BaFe_{0.9}Hf_{0.1}O_3$ |
| 6 | 1 | 0.7 | 0.15 | $BaFe_{0.3}Hf_{0.7}O_3$ |

Figure 6:
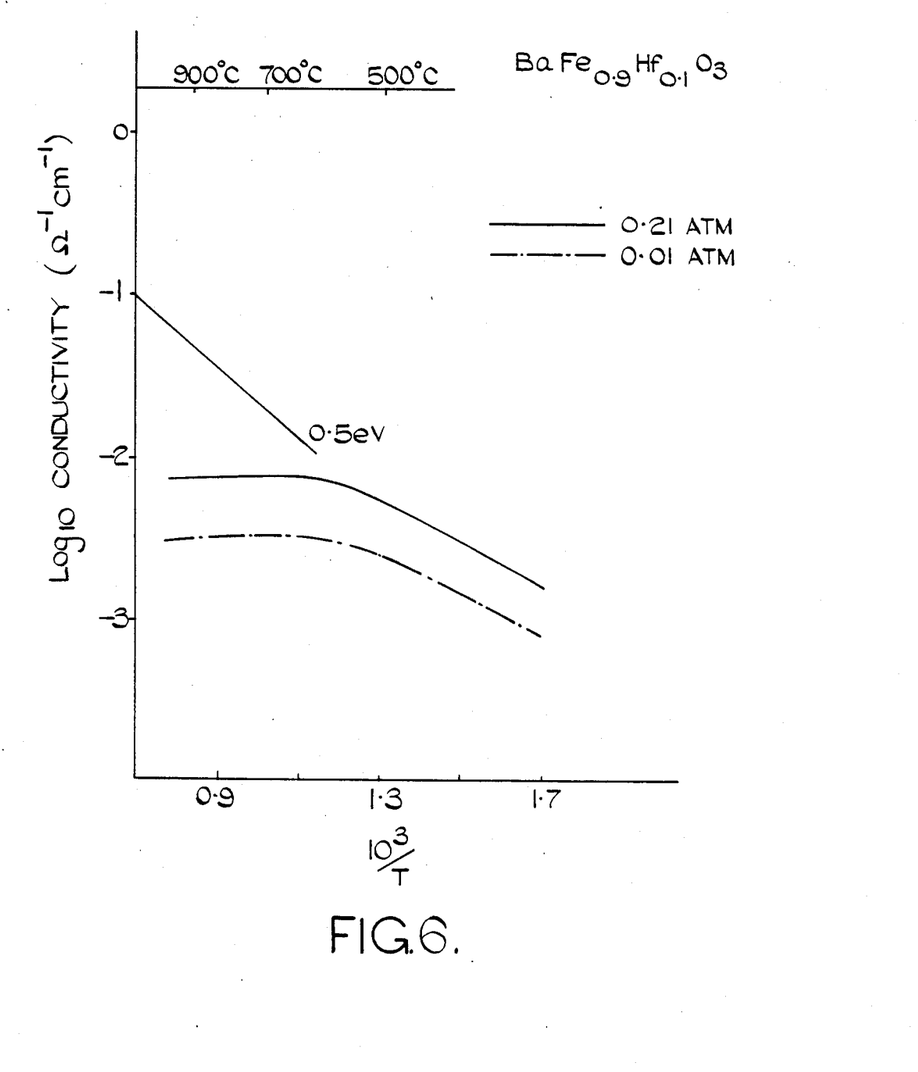
FIG. 6 is a graph as in FIG. 5 for a barium ferrate of composition $BaFe_{0.9}HF_{0.1}O_3$.
Figure 7:
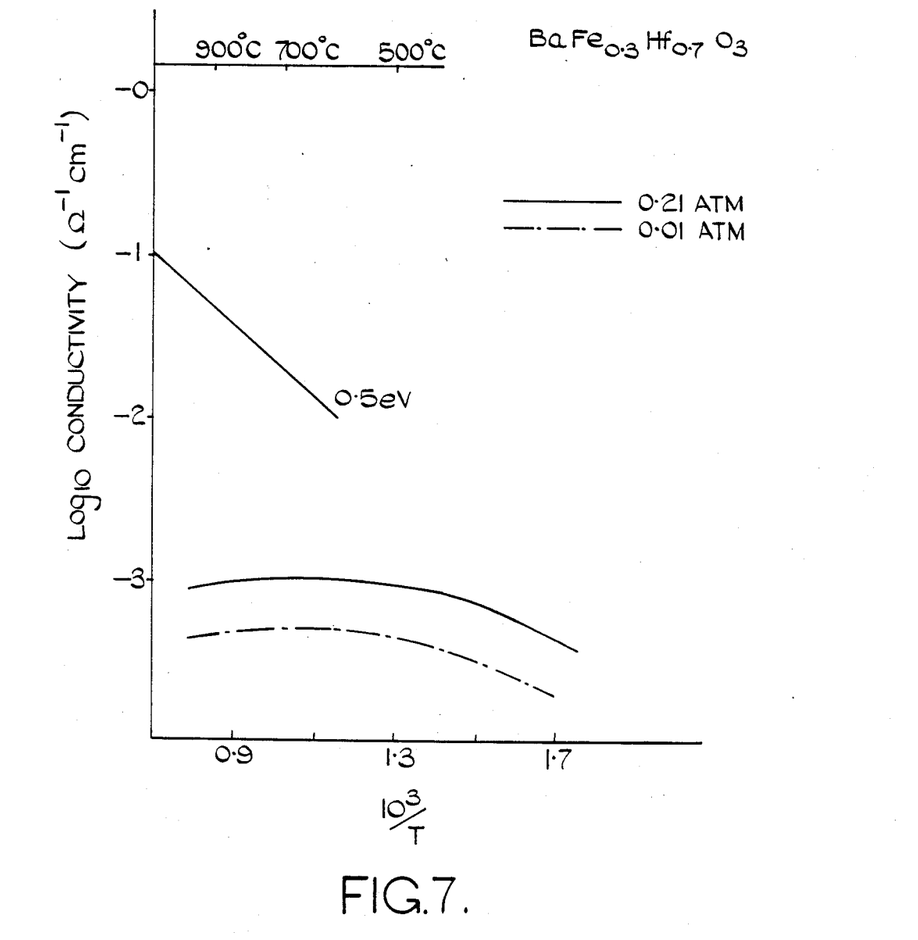
FIG. 7 is a graph as in FIG. 5 for a barium ferrate of composition $BaFe_{0.3}Hf_{0.7}O_3$.

The procedure of Example 4 was repeated with starting materials from different suppliers (and hence having different impurities) but the results obtained showed no significant variation from those shown in FIGS. 5 to 7.

EXAMPLE 7

A powder mixture was prepared consisting of 1 mole of barium carbonate of mean particle size 50 to 70 microns, 0.25 mole of tin oxide again of mean particle size 50 to 70 microns, and 0.375 mole of calcined ferric oxide of mean particle size 25 to 40 microns. Each of the samples was that supplied by British Drug Houses Ltd., as the reagent grade material and, before mixing each sample was subjected to impurity analysis by spark emission spectrography. In the case of the barium carbonate, the main impurities were 0.4% by weight strontium, 150 ppm by weight calcium and 100 ppm by weight silicon, whereas in the case of the tin oxide, the major impurities were 0.15% by weight lead 0.05% by weight arsenic, 250 ppm by weight calcium and 150 ppm by weight silicon. The major impurities in the ferric oxide sample were 0.35% by weight calcium, 0.16% by weight zinc, 0.14% by weight lead, 700 ppm by weight aluminium, 460 ppm by weight nickel, 400 ppm by weight manganese, 280 ppm by weight molybdenum, and 100 ppm by weight tin.

The mixture was ball-milled in the presence of acetone in a synthetic resin pot using alumina balls for 12 hours to obtain a very homogenous mix. The resultant mix was then dried at 100° C. for 2 hours to give a fine, homogenously mixed powder which was ground and then passed through a 75 micron seive. The powder was then placed in an alumina boat in a furnace which was slowly heated (i.e. of the order of up to 10° C. per minute) to 1300° C. in an air atmosphere. The furnace was held at this temperature for 16 hours, whereafter the product so formed was allowed to furnace cool to room temperature before being removed from the furnace. The product removed from the furnace was in the form of agglomerates and was ground before being subjected to X-ray diffraction which showed that tin had entered the ferrate lattice. A sample of the ground powder was then placed in a tool steel die and punch assembly and cold pressed at 345 $MNm^{-2}$ into a cylindrical pellet 10 mm in diameter and 3.8 mm high. After removal from the die the pellet was sintered at 1300° C. for 1 hour and, when the pellet had cooled, electrical contact areas were provided on the planar end surfaces of the pellet. To produce the contact areas, a gold paste was initially applied to the end surfaces, whereafter gold electrodes were attached and the assembly was fired at 1000° C. for four hours to effect joining of the electrodes.

Figure 8:
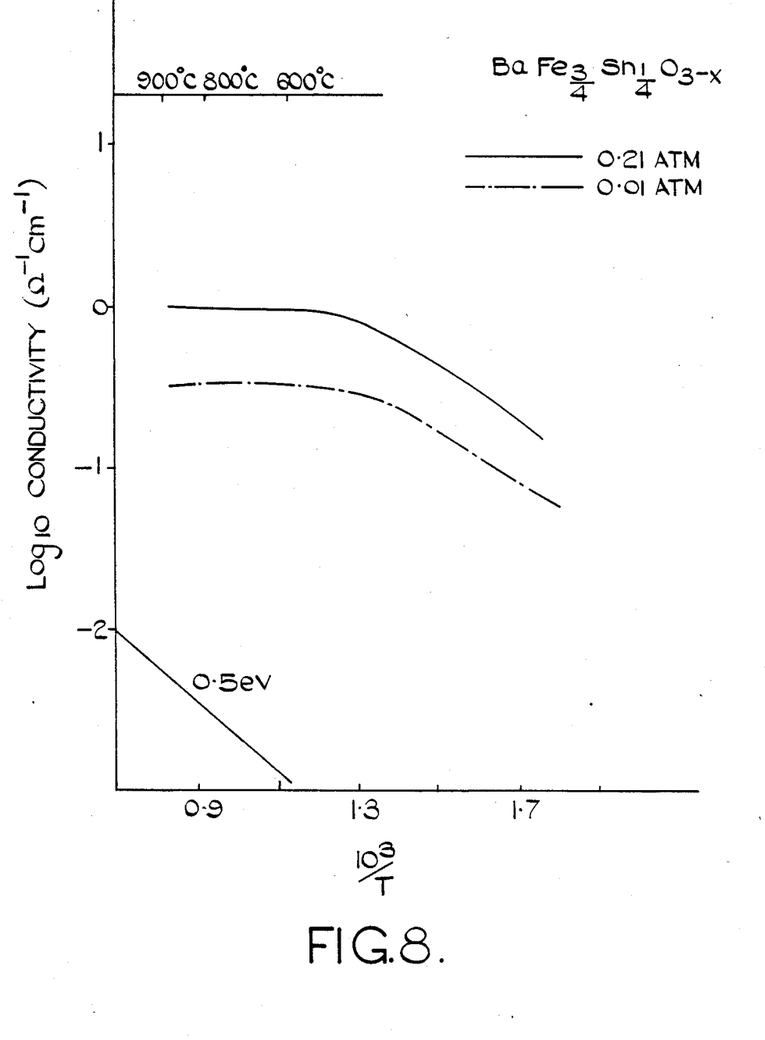
FIG. 8 is a graph plotting log $_{10}$ conductivity (ohm$^{-1}$. cm$^{-1}$) against $10^3$/temperature, T (K) for a barium ferrate of composition $BaFe_{3/4}Sn_{1/4}O_{3-x}$ at different oxygen partial pressures.

The resultant pellet was then mounted in an alumina jig and connected to an LCR bridge to enable electrical conductivity measurements to be made. The jig was then placed in a furnace and, with a constant air atmosphere being maintained in the furnace, the electrical conductivity of the sample was measured at varying temperatures between 300° C. and 1000° C. The results are shown in FIG. 8 by the continuous line numbered 1. The procedure was then repeated with the furnace atmosphere being maintained constant at an oxygen partial pressure of $1\times 10^{-2}$ atm, with the results obtained being shown by the chain dotted line numbered 1 in FIG. 8.

By inspection of the gradient of the lines 1 in FIG. 8, it will be seen that the $E_a$ value for the sample was less than 0.5 eV for both atmospheres and over the entire temperature range investigated. In this respect, it is to be appreciated that the line marked "0.5 ev" is merely intended to show the gradient corresponding to an $E_a$ value of 0.5 eV and hence its position on the graph is arbitrary. It will also be seen from FIG. 8 that, for a given temperature, there was a noticeable difference between the electrical conductivity measured in air (corresponding to an oxygen partial pressure value of 0.21 atm) and the oxygen-depleted atmosphere (i.e. $1\times 10^{-2}$ atm), particularly at the lower temperature in the range investigated.

EXAMPLES 8 AND 9

The procedure described in Example 1 was repeated for mixtures having different relative proportions of tin oxide and ferric oxide so as to vary the amount of tin substitution in a barium ferrate lattice. The composition of these further mixtures and the resultant ferrates are shown in the Table below. The results obtained are shown in FIGS. 9 and 10.

TABLE

| Example No. | $BaCO_3$ mole | $SnO_2$ mole | $Fe_2O_3$ mole | Ferrate |
|---|---|---|---|---|
| 8 | 1 | 0.1 | 0.45 | $BaFe_{0.9}Sn_{0.1}O_3$ |
| 9 | 1 | 0.7 | 0.15 | $BaFe_{0.3}Sn_{0.7}O_3$ |

Figure 9:
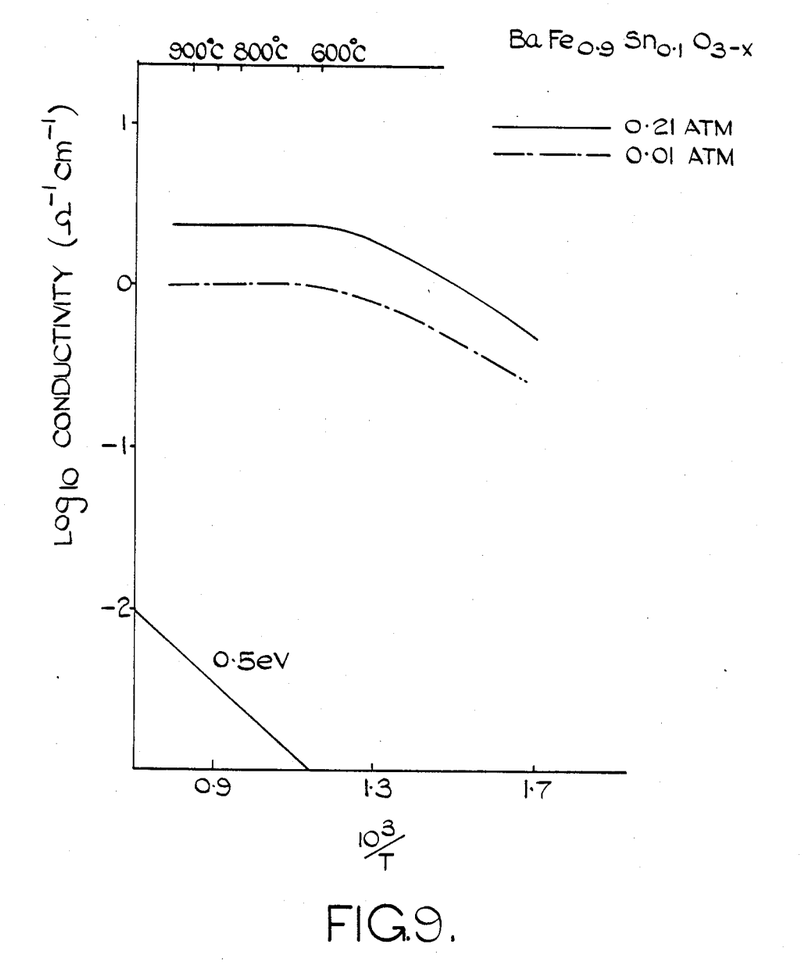
FIG. 9 is a graph as in FIG. 1 for a barium ferrate of composition $BaFe_{0.9}Sn_{0.1}O_3$.
Figure 10:
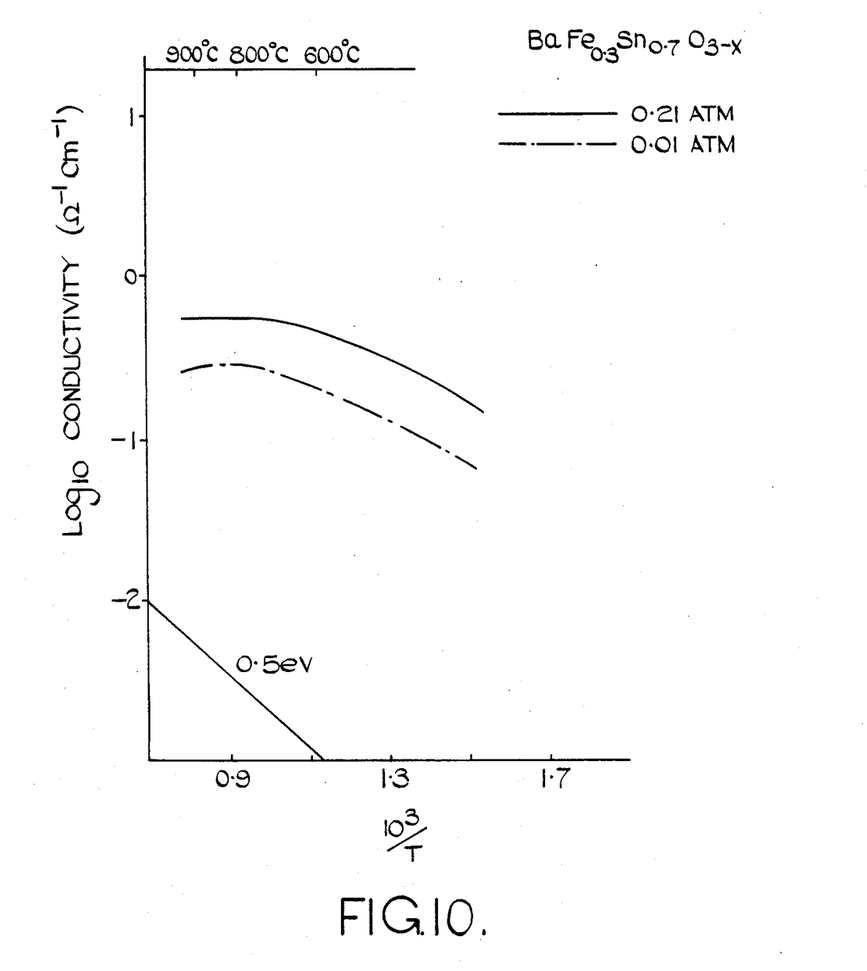
FIG. 10 is a graph as in FIG. 1 for a barium ferrate of composition $BaFe_{0.3}Sn_{0.7}O_3$.

The procedure of Example 7 was repeated with starting materials from different suppliers (and hence having different impurities) but the results obtained showed no significant variation from those shown in the FIGS. 8 to 10.

It can be seen from the Figures that the electrical conductivity of the above Example is significantly lower than those in U.S. Pat. No. 4454494. This decreased conductivity offers either higher voltage signals for different current values, or allows smaller device geometries than previously obtainable.

The sensors of the present invention also exhibit a greater resistance to acid attack than those in U.S. Pat. No. 4454494. This improvement allows greater durability in normal operating conditions.

On thermal cycling the sensors of the above examples, the resistance levels were found to exhibit no variation while those examples given in U.S. Pat. No. 4454494 did show signs of hysteresis of their resistance.

The sensors of the present invention were also found to exhibit insensitivity to temperature fluctuation over a larger temperature range (500° C.-950° C.) as compared with sensors in U.S. Pat. No. 4454494 (600° C.-950° C.). While this improvement may appear small in absolute terms, the improvement in performance for use as a gas sensor is significant.

I claim:

1. An oxygen sensor exhibiting a change in electrical resistance as a function of oxygen partial pressure, comprising at least one of strontium ferrate ($SrFeO_{3-x}$), barium ferrate ($BaFeO_{3-x}$), and strontium barium ferrate ($Sr_{1-b}Ba_bFeO_{3-x}$), where x is a variable and determines the degree of oxygen deficiency of the oxide, and b is 0 to 1, in which part of the iron in the ferrate lattice has been replaced by at least one element selected from the group consisting of zirconium, hafnium and tin.

2. The oxygen sensor according to claim 1, wherein the substituent ferrate obeys the formula: $JFe_{1-y}A_yO_{3-x}$, wherein J is a member selected from the group consisting of Sr, Ba and $Sr_{1-b}Ba_b$, A is at least one element selected from the group consisting of Zr, Hf and Sn, x is a variable and determines the degree of oxygen deficiency of the oxide, y is greater than 0 but less than 0.9, and b is 0 to 1.

3. The oxygen sensor according to claim 2, wherein y is greater than or equal to 0.1 but less than or equal to 0.7.

4. The oxygen sensor according to claim 1, wherein some of said at least one element selected from the group consisting of zirconium, hafnium and tin is substituted by at least one other tetravalent element so that the substituted ferrate obeys the formula: $JFe_{1-y}A_{y-z}D_zO_{3-x}$, wherein J is a member selected from the group consisting of Sr, Ba and $Sr_{1-b}Ba_b$, A is at least one element selected from the group consisting of Zr, Hf and Sn, D is at least one other tetravalent element, y is greater than 0 but less than 0.9, z is less than y, x is a variable and determines the oxygen deficiency of the oxide, and b is 0 to 1.

5. The oxygen sensor according to claim 4, wherein y is greater than or equal to 0.1 bu less than or equal to 0.7.

6. The oxygen sensor according o claim 1, wherein the substituted ferrate has part of the iron replaced by said at least one element selected from the group consisting of zirconium, hafnium and tin and by at least one pentavalent element.

7. The oxygen sensor according to claim 6, wherein said substituted ferrate obeys the formula:

$JFe_{1-y}A_rQ_sO_{3-x}$, wherein J is a member selected from the group consisting of Sr, Ba and $Sr_{1-b}Ba_b$. A is at least one element selected from the group consisting of Zr, Hf and Sn, Q is at least one pentivalent element, y is greater than 0 and less than or equal to 0.5, x is a variable and determines the oxygen deficiency of the oxide, b is 0 to 1, and r+s=y.

8. The oxygen sensor according to claim 6, wherein said at least one element selected from the group consisting of zirconium hafnium and tin, and said at least one pentavelent element are partly replaced by at least one element selected from the group consisting of divalent and trivalent elements.

9. The oxygen sensor according o claim 8, wherein said at least one element selected from the group consisting of divalent and trivalent elements is selected from the group consisting of aluminium, cobalt and nickel.

* * * * *